United States Patent
Nishihama

(10) Patent No.: US 6,949,248 B2
(45) Date of Patent: Sep. 27, 2005

(54) METAL OXIDE/SILICA COMPOSITE, AND A COSMETIC PREPARATION COMPRISING THEREOF

(75) Inventor: Shuji Nishihama, Yokohama (JP)

(73) Assignee: Shiseido Co., Ltd., Tokyo (JP)

( * ) Notice: Subject to any disclaimer, the term of this patent is extended or adjusted under 35 U.S.C. 154(b) by 335 days.

(21) Appl. No.: 10/130,995

(22) PCT Filed: Sep. 25, 2001

(86) PCT No.: PCT/JP01/08308
§ 371 (c)(1),
(2), (4) Date: May 24, 2002

(87) PCT Pub. No.: WO02/24153
PCT Pub. Date: Mar. 28, 2002

(65) Prior Publication Data
US 2003/0068345 A1 Apr. 10, 2003

(30) Foreign Application Priority Data
Sep. 25, 2000 (JP) .................................... 2000-290846

(51) Int. Cl.$^7$ .............................................. A61K 7/48
(52) U.S. Cl. .................... 424/401; 424/59; 424/69; 424/617; 424/642; 424/DIG. 5; 514/944
(58) Field of Search ........................... 424/401, 59, 69, 424/DIG. 5, 617, 642; 514/944

(56) References Cited

U.S. PATENT DOCUMENTS
5,902,569 A * 5/1999 Oshima et al. ............... 424/59

FOREIGN PATENT DOCUMENTS

| JP | 11-001411 A | 1/1999 |
| JP | 11-147809 A | 6/1999 |
| JP | 11-343222 A | 12/1999 |
| JP | 11-349467 A | 12/1999 |

* cited by examiner

*Primary Examiner*—Jyothsna Venkat
(74) *Attorney, Agent, or Firm*—Fei-Fei Chao; Venable LLP

(57) ABSTRACT

The object of this invention is to provide a UV protective powder, and a cosmetic preparation in which the dispersibility of metal oxide is kept at a high level, and the UV protection activity and transparency of the preparation are satisfactorily maintained.

A metal oxide/silica composite wherein metal oxide particles whose primary particle diameter is 1–1000 nm are co-dispersed finely with silica particles, and the metal oxide particles exist substantially as primary particles in the composite. The composite is preferably obtained by mixing (1) a dispersion comprising a silica sol where silica particles have a primary particle diameter of 1–150 nm, and (2) fine particles of metal oxide whose primary particle diameter is 1–1000 nm, or a sol of the same metal oxide, and the metal oxide existing as fine particles or a sol preferably consists of one, or two or more selected from a group consisting of titanium oxide, zinc oxide and cerium oxide. Also a cosmetic preparation comprising thereof is provided.

8 Claims, 5 Drawing Sheets

METAL OXIDE/SILICA COMPOSITE, AND A COSMETIC PREPARATION COMPRISING THEREOF

RELATED APPLICATIONS

This application is 371 of PCT/JP01/08308 filed on Sep. 25, 2001.

This application claims the priority based on Japanese Patent Application No. 2000-290846 filed on Sep. 25, 2000, which is incorporated herein by reference.

BACKGROUND OF THE INVENTION

1. Field of the Invention

The present invention relates to a metal oxide/silica composite and a cosmetic preparation comprising thereof, particularly to an improvement of dispersibility of the metal oxide.

2. Background Arts

When compared with ultra-violet (UV) ray absorbing agents represented by octylmethoxycinnamate, UV protective powders such as titanium oxide or zinc oxide are advantageous in their safety while they are disadvantageous in their giving a whitish shade when applied on the skin, which may cause an artificial finish. To meet this problem, when particles of titanium oxide are coated with a transparent powder such as silica or the like, it is known the transparency of those particles is improved. It is also known that, when ultra-fine particles of titanium oxide or zinc oxide or a sol solution of such a compound is added to a cosmetic preparation, the transparency of the preparation is more emphasized as compared with the same preparation to which a conventional powder of zinc oxide or titanium oxide has been added.

However, when particles of titanium oxide are coated with a transparent powder of silica or the like, the resulting powder tends to lose its UV protection activity in proportion with the increased fraction of the coat. It has been established that, when ultra-fine particles of titanium oxide or of zinc oxide, or a sol solution of such a compound is added to a cosmetic preparation, the particles or the sol settles on the bottom over time, to aggregate there, which may act as a factor responsible for reducing the UV protection activity of the preparation, or for interfering with its stability.

DISCLOSURE OF INVENTION

The object of this invention is to provide a UV protective powder, and a cosmetic preparation in which the dispersibility of metal oxide is kept at a high level, and the UV protection activity and transparency of the preparation are satisfactorily maintained.

The present inventors obtained a gel by directly mixing a fine particle dispersion of metal oxide having a UV protection activity such as titanium oxide, zinc oxide or cerium oxide, or a sol solution of such a compound with a silica sol, in such a manner as to cause them to coagulate. Further, the inventors mixed a fine particle dispersion of the above metal oxide or its sol solution with a silica sol dispersion, under a pH condition where the two sols will not coagulate; then altered the pH by using acid or alkali in such a manner as to cause the two sols to coagulate and deposit, and obtained from the deposit a powder of a composite of the two substances. The inventors discovered that the powder has a structure where silica particles and the metal oxide existing substantially as primary particles intricately intermingle with each other (finely co-disperse), and has a high transparency and UV protection activity. Finally, the inventors discovered that a sun-screen supplemented with a powder of this composite gives a natural finish free from the artificial whitish shade when applied on the skin, while keeping a high UV protection activity, and completed this invention.

The metal oxide/silica composite of this invention is characterized by having a structure where metal oxide particles whose primary particle diameter is 1–1000 nm and existing substantially as primary particles in the composite co-disperse finely with silica particles.

The metal oxide/silica composite of this invention is preferably obtained by mixing (1) a dispersion comprising a silica sol where silica particles have a primary particle diameter of 1–150 nm, and (2) fine particles of metal oxide whose primary particle diameter is 1–1000 nm, or a sol of the same metal oxide.

Alternatively, the metal oxide/silica composite of this invention is preferably obtained by mixing the above dispersion with fine particles of metal oxide or its sol, and altering the pH of the resulting mixture solution, so as to cause the silica and the metal oxide to aggregate for deposition.

Still further, for producing the metal oxide/silica composite of this invention, the metal oxide existing as fine particles or a sol preferably consists of one, or two or more selected from a group consisting of titanium oxide, zinc oxide and cerium oxide.

Still further, for producing the metal oxide/silica composite of this invention, the metal oxide/silica composite exists as a gel-like composition.

Still further, the metal oxide/silica composite of this invention is obtained by drying the gel-like composition to a powdery composition.

Still further, the metal oxide/silica composite of this invention preferably comprises 5–90 wt % metal oxide with respect to the total weight of the composite.

Still further, the cosmetic preparation of this invention is characterized by comprising such a metal oxide/silica composite.

BEST MODE FOR CARRYING OUT THE INVENTION

Figure 1:
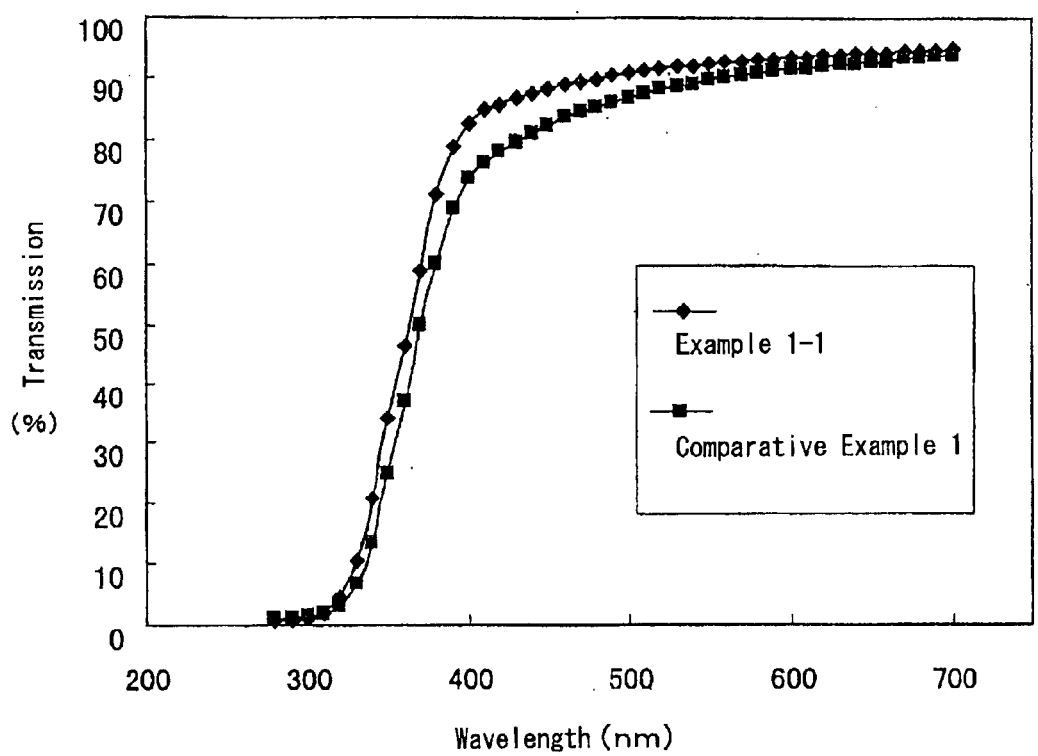
FIG. 1 is a graph to show the optical transmissions of a composite of titanium oxide/silica (Example 1) and of Comparative Example 1.

The detailed description of this invention will be given below.

The silica sol included in the present invention is a system in which fine silica colloid particles are uniformly dispersed in a medium. The commercially available such system may include "Snowtex" series provided by Nissan Chemical Industries, Ltd. The dispersing medium may include any solvent including water, isopropanol, methylethylketone, etc., as long as the solvent does not interfere with the dispersion stability of silica particles in the sol. If water is employed as the dispersing medium, it is possible to control the development of a metal oxide/silica composite so as to produce a highly functional commposite in which particles are more uniformly dispersed than otherwise possible, by choosing an acidic or alkaline silica sol solution in accordance with the iso-potential point of metal oxide to be mixed which may exist as particles or as a sol.

Particles of silica in a sol used in this invention have a diameter of 1–150 nm, preferably 5–100 nm. If the particles had a larger diameter or a smaller diameter than the above range, those silica particles could not smoothly invade the interstices between titania particles, and thus could not disperse the titania particles uniformly. As a result, titania particles would aggregate themselves while silica particles aggregate themselves, and the resulting cosmetic preparation would have a reduced UV protection activity, and give a notable artificial white appearance when applied on the skin.

The particulate or sol metal oxide mentioned in this invention may include one, or two or more selected from a group consisting of titanium oxide, zinc oxide and cerium oxide. The metal oxide existing as particles or as a sol may be obtained as a solid solution consisting of two or more selected from a group consisting of titanium oxide, zinc oxide and cerium oxide, or as a solid solution consisting of a metal oxide as above with another metal oxide. The primary particles of metal oxide have a diameter of 1–1000 nm, preferably 5–500 nm. If the primary particles of metal oxide had a larger diameter than the above range, they would have a reduced tendency for forming a composite with a silica sot, and a reduced UV protection activity by an amount corresponding with the incremental addition of silica. If the primary particles of metal oxide had a smaller diameter than the above range, the resulting composite would not give a cosmetic preparation with a high UV protection activity.

A general acidic or alkaline agent can be employed in the invention as a pH adjusting agent for gelation of the metal oxide/silica composite. As examples of such an acidic agent, hydrochloric acid, acetic acid, citric acid, sulfuric acid, phosphoric acid, nitric acid and the like are illustrated. Also as examples of such an alkaline agent, sodium hydroxide, potassium hydroxide, sodium carbonate, potassium carbonate, aqueous ammonia and the like are illustrated.

The fraction of metal oxide in the metal oxide/silica composite of this invention is 5–90 wt. %, preferably 25–80 wt. % with respect to the total weight of the composite. If the fraction were below the above range, no cosmetic preparation based on the composite would give a desired UV protection activity. If the fraction were over the above range, particulate or sol metal oxide would aggregate solely by themselves, and a cosmetic preparation based on the composite would have a reduced UV protection activity contrary to expectation.

The composite is dried being heated at room temperature to 200° C., preferably in a range of 80–120° C. Drying a composite causes silica colloids in the sol to be condensed, and titania fine particles to be stably dispersed throughout the sol to be held there. Therefore, it is desirable to develop a composite while preventing silica sol from maintaining an initial state.

In the process obtaining a composite of metal oxide or its sol, and silica sol, the other kind of metal oxide or its sol is also incorporated and mixed with them at the same time to obtain a composite with them. For example, metal oxides or sol thereof such as aluminum oxide(alumina), iron oxide, copper oxide, magnesium oxide, nickel oxide, zirconium oxide, cobalt oxide and the like can be incorporated to obtain the composite with them. Also metal fine particles of such as gold colloid particles can be incorporated to obtain the composite with them.

A composite of metal oxide/silica obtained by the invention can be used with a hydrophobic treatment by a fatty acid salt such as aluminum stearate, zinc myristate; a fatty acid such as stearic acid, palmitic acid; a wax such as candelilla wax, carnauba wax; modified silicone such as polyoxyethylene modified silicone, carboxyl modified silicone, amino modified silicone; silicone oil such as methyl polysiloxane, methylphenyl polysiloxane; dextrin fatty acid ester and the like at need.

In a cosmetic preparation of the invention, constituents normally employed for a cosmetic preparation can be contained in such a manner that the effect of the invention is not lost. For example, a solid or semi-solid oil such as petrolatum, lanolin, ceresin, carnauba wax, candelilla wax and higher alcohol; a liquid oil such as squalane, liquid petrolatum and ester oil; an oil such as silicone oil; a humectants such as sodium hyaluronate and glycerin; a surfactant such as cationic surfactant and non-ionic surfactant; and a pigment, an antiseptic, a perfume, an invigorate agent are suitably contained.

The present invention will be described in detail below by means of Examples and Comparative Examples, but the scope of this invention should not be limited in any way to those Examples. The inventors manufactured powders having UV protection activities as represented by Examples 1 to 5 and Comparative Examples 1 to 4 described below. Examples represent mixtures including silica sols, while Comparative Examples corresponding mixtures with no silica sol added.

EXAMPLE 1-1

A 50 g of Snowtex O (silica sol available from Nissan Chemical Industries, Ltd. which contains 20% silica, and in which silica primary particles have a diameter of 10–20 nm) and 10 g of TSK-5 (titania sol available from Ishihara Sangyo Kaisha, Ltd. which contains 30% titanium oxide particles rutile type having a primary diameter of 10–100 nm) were mixed; to the resulting uniform dispersion was added dropwise 0.1M aqueous solution of sodium hydroxide to bring pH=9; and then a gel-like substance was obtained. The substance was filtered and washed with water five times or more; and the resulting solid was exposed to a temperature of 100 to 110° C., to cause moisture to be evaporated. Thus, a powder comprising a composite of titanium oxide/silica was obtained.

EXAMPLE 1-2

A 15 g of Snowtex O (silica sol available from Nissan Chemical Industries, Ltd. which contains 20% silica, and in which silica primary particles have a diameter of 10–20 nm) and 268 ml of titania sol aquesous solution (which has pH=1, and contains 8 g of $TiO_2$ anatase type which has a primary particle diameter of 10–100 nm) were mixed; to the resulting uniform dispersion was added dropwise 0.1M aqueous solution of potassium hydroxide to bring pH=8.5; and then a gel-like substance was obtained. The substance was filtered and washed with water five times or more; the resulting solid was exposed to a temperature of 90° C., to cause moisture to be evaporated. Thus, a powder comprising a composite of titanium oxide/silica was obtained.

EXAMPLE 1-3

A 40 g of Snowtex O (silica sol available from Nissan Chemical Industries, Ltd. which contains 20% silica, and in which silica primary particles have a diameter of 10–20 nm) and 268 ml of titania sol aquesous solution (which has pH=1, and contains 8 g of TiO2 anatase type which has a primary particle diameter of 10–100 nm) were mixed; to the resulting uniform dispersion was added dropwise 0.1M aqueous solution of potassium hydroxide to bring pH=8.5; and then a gel-like substance was obtained. The substance was filtered and washed with water five times or more; and the resulting solid was exposed to a temperature of 90° C., to cause moisture to be evaporated. Thus, a powder comprising a composite of titanium oxide/silica was obtained.

EXAMPLE 2

A 100 g of Snowtex 30 (silica sol available from Nissan Chemical Industries, Ltd. which contains 30% silica, and in which silica primary particles have a diameter of 10–20 nm) and 10 g of TSK-5 were mixed; to the resulting dispersion was added dropwise 0.5M diluted aqueous solution of hydrochloric acid to bring pH=7–8; and then a gel was obtained. The gel was filtered and washed with water five times or more; and the resulting solid was exposed to a temperature of 100 to 110° C. for drying. Thus, a powder comprising a composite of titanium oxide/silica was obtained.

EXAMPLE 3

A powder of zinc oxide as described in an Example of WO99/25654 (which has a primary particle diameter of 50–100 nm) was allowed to disperse in Snowtex XL (silica sol available from Nissan Chemical Industries, Ltd., which contains 40% silica, and in which silica primary particles have a diameter of 40–60 nm) to give a ratio of silica sol: zinc oxide=25:75. To the dispersion was added 0.1M diluted aqueous solution of hydrochloric acid to give a gel-like substance which was then dried and pulverized. The resulting powder was washed with water and dried again. Thus, a powder of a composite of zinc oxide/silica was obtained.

EXAMPLE 4

A dispersion comprising silica sol/isopropyl alcohol (IPA-ST, 30% silica content, primary particle diameter of 10–20 nm) was mixed with a sol of cerium oxide (primary particle diameter of 50–100 nm) to give a ratio of silica gel:cerium oxide=35:65. The resulting dispersion was dried while being stirred with a kneader. Thus, a powder of a composite of cerium oxide/silica was obtained.

EXAMPLE 5

A 15 g of Snowtex O (silica sol available from Nissan Chemical Industries, Ltd.) and 30 g of alumina sol 100 (which contains 10–11% alumina) were mixed. To the mixture was added 100 g of titania sol (TSK-5), and to the resulting uniform dispersion was added dropwise 0.2M aqueous solution of sodium hydroxide to bring pH=7, which produced a gel-like substance. The substance was filtered and washed with water five times or more; and the resulting solid was exposed to a temperature of 100–110° C., to cause moisture to be evaporated. Thus, a powder comprising a composite of titanium oxide/silica/alumina was obtained.

COMPARATIVE EXAMPLE 1

Particulate titanium oxide (titanium oxide 100AL, available from Tayca Corporation, primary particle diameter of 30 nm) and Aerosil #200 (silica gel available from Nippon Aerosil Co., Ltd., primary particle diameter of 12 nm) were mixed to give a ratio of 3:1, and the yield was stirred for 1 minute with a mixer. The resulting preparation was used as Comparative Example 1.

COMPARATIVE EXAMPLE 2

To a solution which had been obtained by dissolving 30 g of aqueous glass in 150 g of water was added 100 g of titania sol (TSK-5). To the resulting solution was added 0.5M diluted aqueous solution of hydrochloric acid to bring pH=7–8. The yield was dried by heating, while being stirred with a kneader. The resulting powder was washed with water, dried and pulverized. The yield was used as Comparative Example 2.

COMPARATIVE EXAMPLE 3

A 20 g of sodium metasilicate was dissolved in 300 g of water; to the resulting solution was added a powder of zinc oxide as described in an Example of WO99/25654 for dispersion; and to the resulting solution was added 1M diluted aqueous solution of hydrochloric acid to bring pH=8. The resulting dispersion was filtered, washed and dried to give a powder which was used as Comparative Example 3.

COMPARATIVE EXAMPLE 4

A cerium sol and tetraethylorthosilicate were mixed to give a ratio of cerium oxide:silica=65:35. The mixture was heated at 80° C. for 12 hours for hydrolysis. The reaction product was filtered, washed, dried and pulverized. The yield was used as Comparative Example 4.

The present inventors made following comparison experiments using the above powders.

Comparison Experiment 1-1

The inventors compared Example 1-1, a powder of a titanium oxide/silica composite of this invention, with Comparative Example 1, a powder of a blend of titanium oxide particles and silica particles.

The powders of Example 1-1 and Comparative Example 1 were added to castor oil to give a ratio of powder:castor oil=1:9. From each mixture, a slurry comprising the powder and castor oil was prepared. The slurry was kneaded with a kneader based on three rollers. After kneading, the slurry was applied on a quartz plate with an applicator to produce a film of 5 $\mu$m thickness thereupon. The UV transmission through the film was measured with a spectrophotometer (U-3410, Hitachi, Ltd.).

FIG. 1 shows the measurement results of the slurry obtained in the Comparison Experiment 1. Comparison of the results in FIG. 1 shows that, although the transmission through Example 1-1 of UVB having a wavelength of 290–320 nm is practically the same with the counterpart for Comparative Example 1, the transmission through Example 1-1 of rays having a visible wavelength is generally higher than the counterpart for Comparative Example 1. This suggests Example 1-1, when compared with Comparative Example 1, has a similar UV protection activity but a higher transparency to visible rays, thus being capable of exercising a higher cosmetic function which may be ascribed to the more intimate integration of titanium oxide particles with silica particles.

As in Comparative Example 1, Examples 1-2 and 1-3, each comprising a titanium oxide/silica composite obtained from a titanium oxide sol and a silica sol, were added to castor oil to give slurries. The slurry was allowed to form a thin film. The transmission of UV rays through the film was measured with a spectrophotometer (U-3410, Hitachi).

Figure 2:
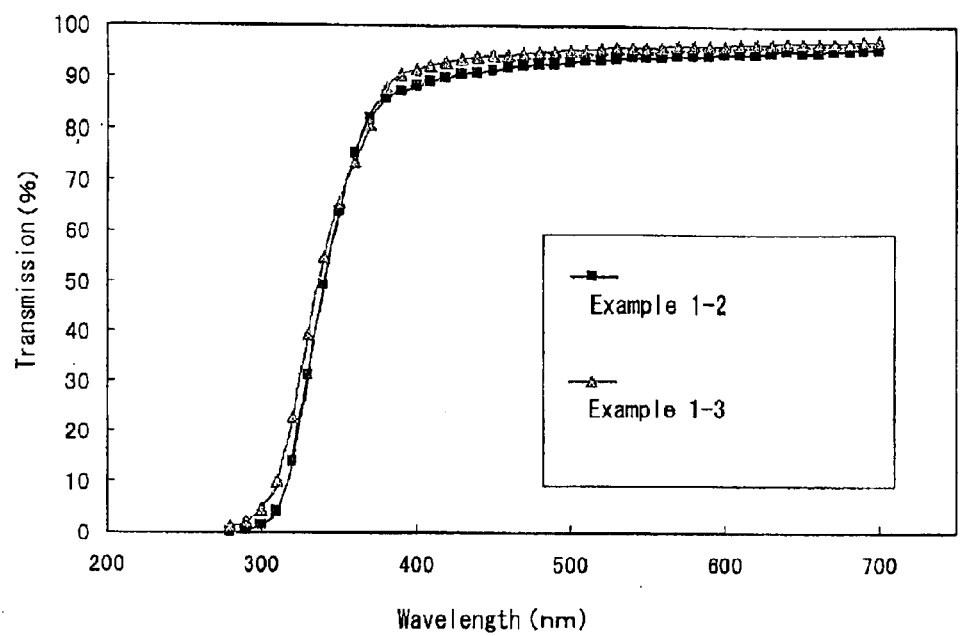
FIG. 2 is a graph to show the optical transmissions of two composite of titanium oxide/silica (Examples 1-2 and 1-3).

FIG. 2 shows the measurement results. It is seen from the figure that both of Examples 1-2 and 1-3 give powders as excellent in protecting against UV rays, and in transparency as Example 1-1 owing to the intimate integration of titanium oxide particles with silica particles.

X-Ray Diffraction Pattern of the Commposite

Figure 3:
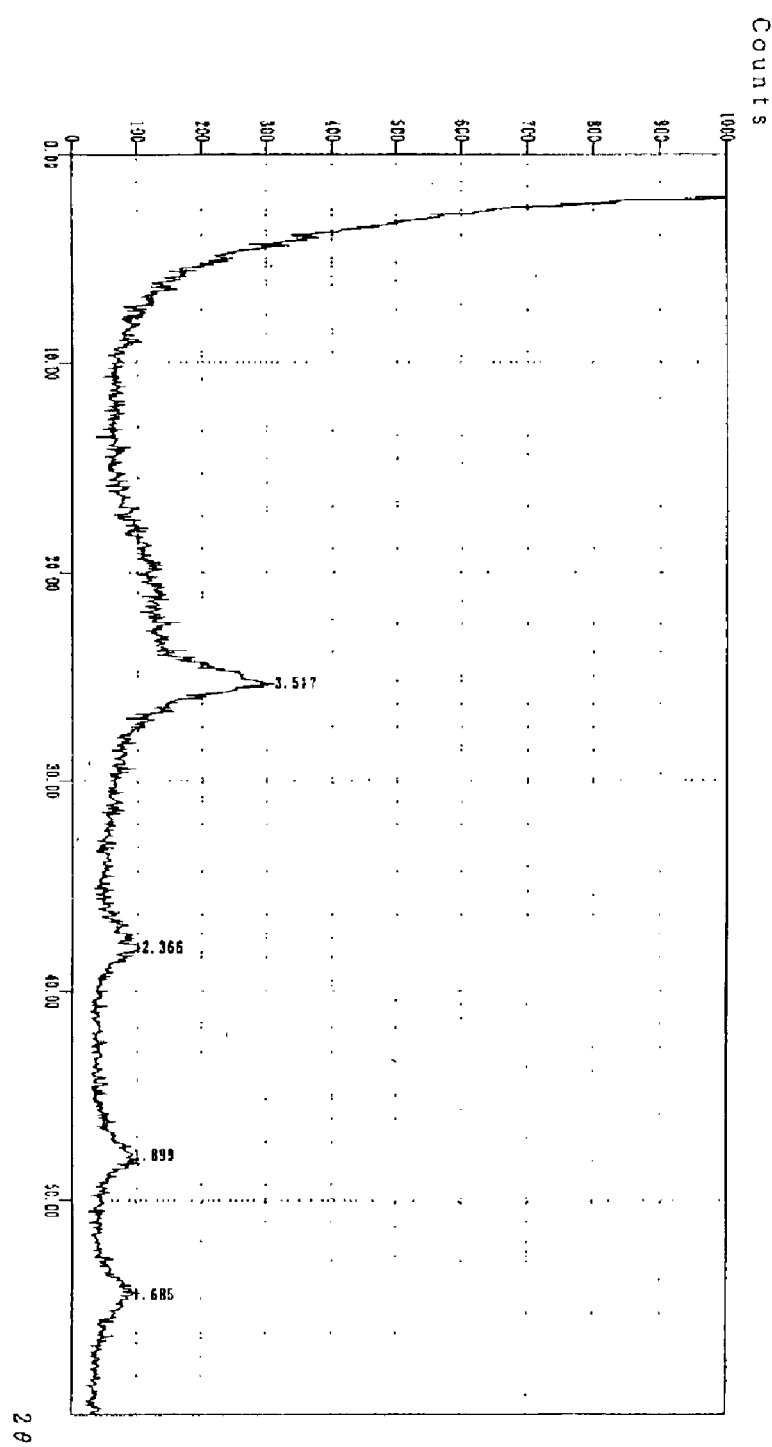
FIG. 3 is a chart to show an X-ray diffraction pattern of a composite of titanium oxide/silica (Example 1-2).

Next, the inventors applied an X-ray analysis to the metal oxide/silica composite. FIG. 3 shows an X-ray diffraction pattern of a titanium oxide/silica composite represented by Example 1-2. From the result shown in FIG. 3, it is seen that titanium oxide does not give any notable peak excepting a main peak. This suggests that titanium oxide exists, in the titanium oxide/silica composite, substantially as primary particles dispersed therethrough.

The Content of Metal Oxide in the Composite

The inventors prepared titanium oxide/silica composite having compositions as described in Table 1 below, and studied how the content of metal oxide affects the performance of the composite. In accordance with Comparison Experiment 1, the transmission of rays therethrough at a wavelength of 310 nm was measured. The UV protection activity of the film was evaluated and ranked as follows.

(Ranking of the Protection Activity)

⊚: Transmission at 310 nm is less than 10%.
◯: Transmission at 310 nm is not less than 10% but less than 20%.
Δ: Transmission at 310 nm is not less than 20% but less than 30%
X: Transmission at 310 nm is not less than 30%.

TABLE 1

| amount of titanium oxide (wt. %) | amount of silica (wt. %) | UV protection activity |
|---|---|---|
| 1 | 99 | X |
| 5 | 95 | ◯ |
| 10 | 90 | Δ |
| 30 | 70 | ◯ |
| 50 | 50 | ⊚ |
| 75 | 25 | ⊚ |
| 85 | 15 | ◯ |
| 90 | 10 | ◯ |
| 95 | 5 | Δ |

From the results of Table 1, it is seen that the content of metal oxide in the metal oxide/silica composite should be 5–90 wt. %, preferably 25–80 wt. %.

Next, the inventors studied the relationship between the content of titanium oxide in a titanium oxide/silica composite and the half-value width for d=3.25 (peak representing a (hk1)=(110) surface of rutile type titanium oxide).

TABLE 2

| content of titanium oxide | the half-value width for d = 3.25 (100% titanium oxide is normalized to be 1.) |
|---|---|
| 17% | 1.40 |
| 60% | 1.22 |
| 88% | 1.11 |
| 100% | 1.00 |

From the results of Table 2 it is seen that the half-value width increases with the reduction of titanium oxide content in the composite, suggesting the crystalline nature of titanium oxide is impaired. This suggests that titanium oxide exists, in the titanium oxide/silica composite, substantially as primary particles dispersed therethrough.

Figure 4:
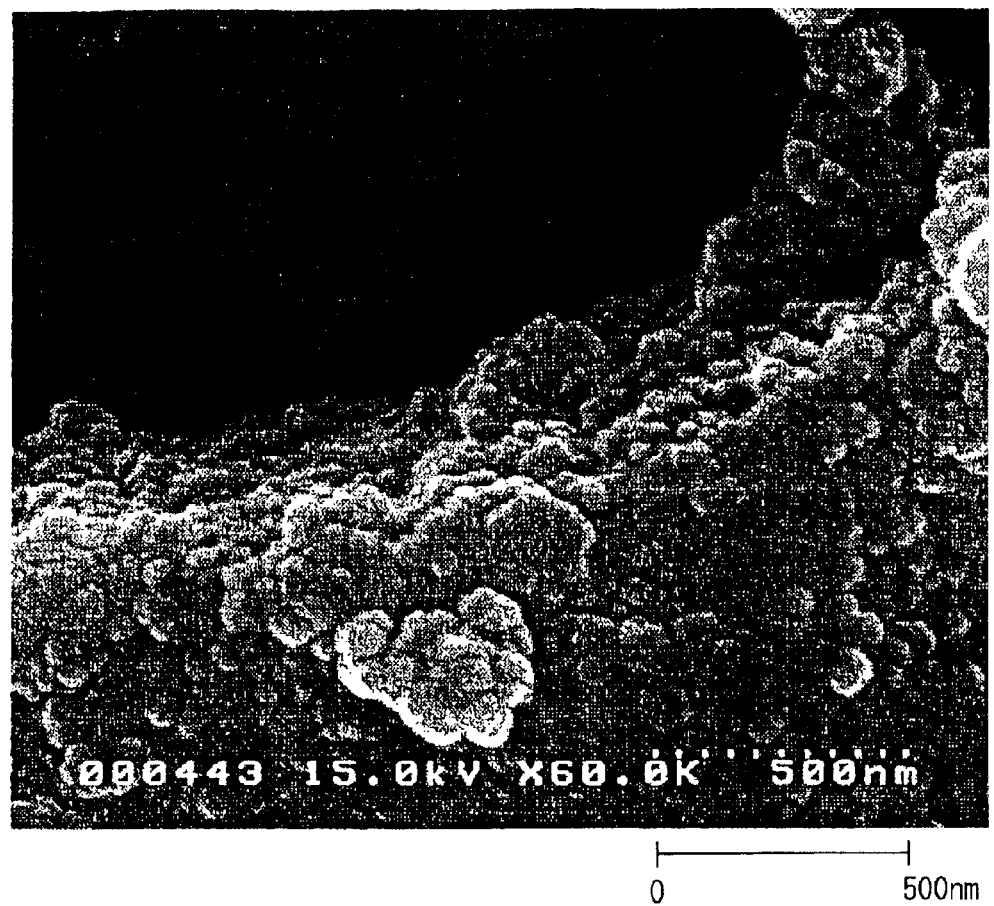
FIG. 4 is an SEM (scanning electron microscopy) photomicrograph of a composite of titanium oxide/silica.
Figure 5:
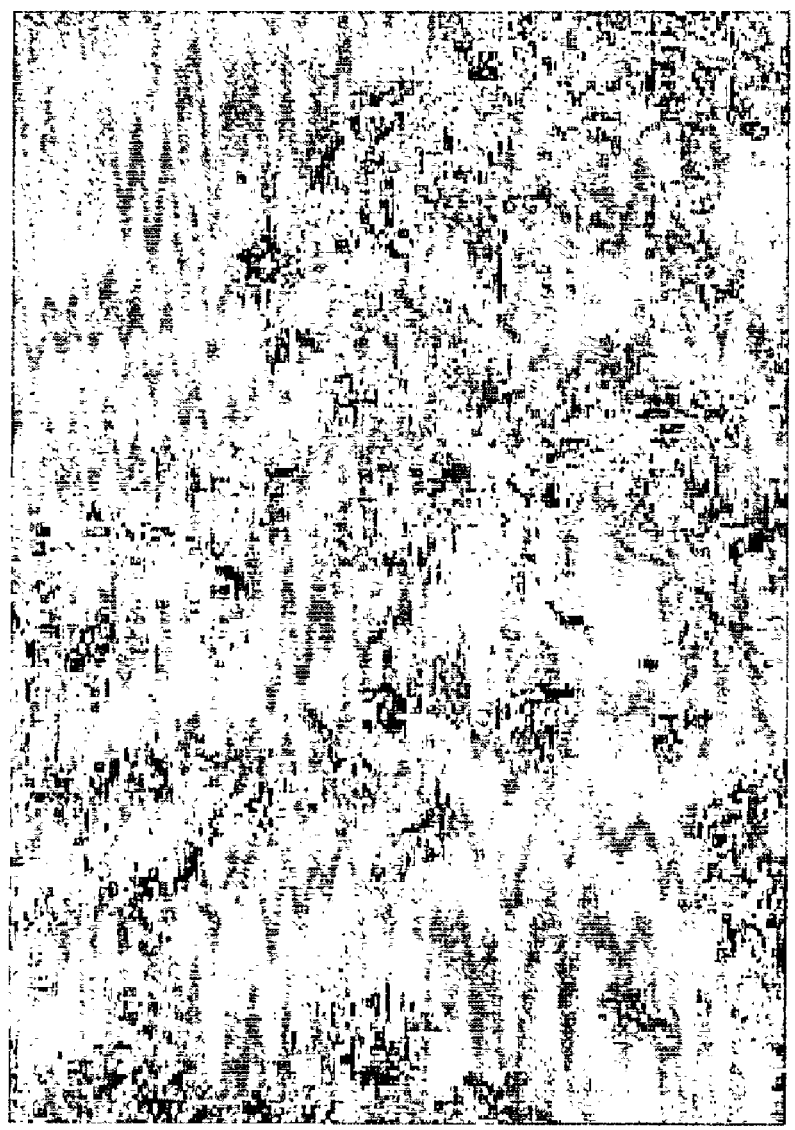
FIG. 5 is a TEM (transmission electron microscopy) photomicrograph of a composite of titanium oxide/silica.

FIG. 4 shows an SEM photomicrograph of a titanium oxide/silica composite of this invention (Example 1-2). From FIG. 4 it is confirmed that titanium oxide and silica exist substantially as primary particles, and intermingle with each other to give a uniform dispersion.

Specific Surface Area of the Composite

Next, the inventors studied the specific surface area of a titanium oxide/silica composite. The results are shown in Table 3. The results obtained from the constituents are listed under (1) and (2), the result from the composite under (3) and a theoretical value expected for the composite under (4).

TABLE 3

| | | specific surface area ($m^2/g$) |
|---|---|---|
| (1) | dried titania sol | 265.7 |
| (2) | silica sol | 239.8 |
| (3) | the titanium oxide/silica composite of the invention (titanium oxide:silica = 70:30) | 291.3 |
| (4) | the titanium oxide/silica composite via calculation from (1) and (2) | 257.9 |

From the results of Table 3, it is seen that the measured specific surface area of the titanium oxide/silica composite is larger than the theoretical counterpart of the same composite obtained via calculation using the corresponding values of its constituents, i.e., titania sol and silica sol. It can be said from this that the two kinds of particles intimately mix with each other to form a uniform composite which rather prevents the two kinds of particles from agglutinating to each other.

Comparison Experiment 2

The inventors prepared O/W emulsified sunscreens using the powders obtained in Example 2 and in Comparative Example 2. Then, they compared the cosmetic preparations containing the powdery composites prepared from a titanium oxide sol and a silica sol as in Example 2, and the cosmetic preparations containing powdery mixtures prepared without using a silica sol as in Comparative Example 2. The prescription of the experimental cosmetic preparation is as shown in Table 4, and its preparation process is given below.

TABLE 4

| | Example 6 O/W emulsified sunscreen | |
|---|---|---|
| 1. | Powder of Example 2 | 12 |
| 2. | Zinc white | 5 |
| 3. | Stearic acid | 2 |
| 4. | Cetyl alcohol | 1 |
| 5. | Petroleum | 5 |
| 6. | Silicone oil | 2 |
| 7. | Liquid petroleum | 10 |
| 8. | Glyceryl monostearate (self-emulsifying type) | 1 |
| 9. | Polyoxyethylene (25 mol) mono oleate | 1 |
| 10. | Polyethyleneglycol 1500 | 5 |
| 11. | Beegum | 0.5 |
| 12. | Purified water | 55.5 |
| 13. | Perfume | suitable amount |
| 14. | Antiseptic | suitable amount |

Preparation Process

To constituent 12 was added constituent 10, which was dissolved by heating, and constituent 11 was added, and the mixture was stirred with a homomixer to give a uniform dispersion, which was then maintained at 70° C. The yield was used as a water phase. Constituents 3–9 were mixed with constituents 13 and 14, which was then heated for dissolution and maintained at 70° C. To the water phase were added powders of constituents 1 and 2, and were dispersed with a homomixer. To this dispersion was added the oil phase, which was uniformly emulsified with a homomixer.

After emulsification, the emulsion was cooled to 35° C. while being stirred. Thus, a sunscreen of Example 6 was obtained.

The same process as used to produce the O/W emulsified sunscreen of Example 6 was employed, except that a powder obtained in Comparative Example 2 was used, instead of a powder obtained in Example 2, to give a powder of Comparative Example 5. Example 6 and Comparative Example 5 were applied to the skin, and the resulting stains were evaluated by vision for how notable their whiteness is. The evaluation was ranked as follows. The results are shown in Table 5.

(Ranking of Transparency)
○: transparency present
Δ: somewhat notable whiteness, and slightly low transparency
X: notable whiteness, and no transparency

TABLE 5

|  | Example 6 | Comparative Example 5 |
|---|---|---|
| Transparency | ○ | Δ |

From the results of Table 5 it is seen that Example 6 including a composite comprising titanium oxide of Example 2 as primary particles and silica particles both of which disperse intimately into each other, provides a sunscreen whose whiteness looks natural and plain even when observed immediately after its application to the skin, and thus ensures a fine finish. In contrast, Comparative Example 5 containing a powder of Comparative Example 2 gives a notable white when applied to the skin. Moreover, it is more difficult to extend Comparative Example 5 uniformly over the skin. From this it is obvious that if silica sol were not added during the manufacture of a composite, particles of titanium oxide could not disperse to the same extent as observed in the composite of this invention.

Comparison Experiment 3

The inventors prepared oily stick foundations using powders obtained in Example 3 and in Comparative Example 3. Thus, they compared a cosmetic preparation obtained from a powder of this invention prepared in Example 3, i.e., a composite prepared from particulate zinc oxide and a silica sol, with a cosmetic preparation based on a powder prepared in Comparative Example 3, i.e., a similar composite with, however, no silica sol added. The prescription of the experimental cosmetic preparation is as shown in Table 6, and its preparation process is given below.

TABLE 6

Example 7 Oily stick foundation (Powder Part)

| 1. | Powder of Example 3 | 8 |
|---|---|---|
| 2. | Talc | 2.8 |
| 3. | Kaolin | 16 |
| 4. | Mica | 3 |
| 5. | Titanium dioxide | 16 |
| 6. | Red iron oxide | 1 |
| 7. | Yellow iron oxide | 3 |
| 8. | Black iron oxide | 0.2 |

(Oil Part)

| 9. | Solid Parrafin | 3 |
|---|---|---|
| 10. | Microcrystalline wax | 7 |
| 11. | Petroleum | 15 |
| 12. | Dimethyl polysiloxane | 3 |

TABLE 6-continued

Example 7 Oily stick foundation

| 13. | Squalane | 5 |
|---|---|---|
| 14. | Isopropyl palmitate | 17 |
| 15. | Antioxidant | suitable amount |
| 16. | Perfume | suitable amount |

Preparation Process

Constituents 9–15 were kept at 85° C. for dissolution, to which was added a powder well mixed with stirring. The yield was then pulverized with a colloidal mill for dispersion. Then, constituent 16 was added to the mixture, and the resulting yield, after deaeration, was poured into a vessel at 70° C., and cooled to give a foundation of Example 7.

The same process as used to produce the oily stick foundation of Example 7 was employed, except that a powder obtained in Comparative Example 3 was used, instead of a powder obtained in Example 3, to give a preparation of Comparative Example 6.

Example 7 and Comparative Example 6 were applied to the skin, and the resulting stains were evaluated immediately after application by vision for how notable their whiteness is. The evaluation was ranked as above. The results are shown in Table 7.

TABLE 7

|  | Example 7 | Comparative Example 6 |
|---|---|---|
| Transparency | ○ | Δ |

From the results of Table 7 it is seen that Example 7 comprising a composite of titanium oxide of Example 3 provides a foundation whose whiteness looks natural and plain even when observed immediately after its application to the skin, and thus ensures a fine finish. In contrast, Comparative Example 3 containing a powder of Comparative Example 3 gives a notable white when applied to the skin. Moreover, it is more difficult to extend Comparative Example 6 uniformly over the skin. From this it is obvious that addition of silica sol improves the dispersibility of zinc oxide as well as of titanium oxide.

Comparison Experiment 4

The inventors prepared oily stick foundations using powders obtained in Example 4 and in Comparative Example 4. The prescription of the experimental cosmetic preparation is as shown in Table 8, and its preparation process is given below.

The inventors prepared oily stick foundations using powders obtained in Example 4 and in Comparative Example 4. Then, they compared a cosmetic preparation obtained from a powder of this invention prepared in Example 3, i.e., a composite prepared from a cerium oxide sol and a silica sol, with a cosmetic preparation based on a powder prepared in Comparative Example 4, i.e., a similar composite with, however, no silica sol added. The prescription of the experimental cosmetic preparation is as shown in Table 8, and its preparation process is given below.

TABLE 8

Example 8 Oily stick foundation (Powder Part)

| | | |
|---|---|---|
| 1. | Powder of Example 4 | 8 |
| 2. | Talc | 2.8 |
| 3. | Kaolin | 16 |
| 4. | Mica | 3 |
| 5. | Titanium dioxide | 16 |
| 6. | Red iron oxide | 1 |
| 7. | Yellow iron oxide | 3 |
| 8. | Black iron oxide | 0.2 |

(Oil Part)

| | | |
|---|---|---|
| 9. | Solid Parrafin | 3 |
| 10. | Microcrystalline wax | 7 |
| 11. | Petroleum | 15 |
| 12. | Dimethyl polysiloxane | 3 |
| 13. | Squalane | 5 |
| 14. | Isopropyl palmitate | 17 |
| 15. | Antioxidant | suitable amount |
| 16. | Perfume | suitable amount |

Preparation Process

Constituents 9–15 were kept at 85° C. for dissolution, to which was added a powder well mixed with stirring. The yield was then pulverized with a colloidal mill for dispersion. Then, constituent 16 was added to the mixture and the yield, after deaeration, was poured into a vessel at 70° C., and cooled to give a foundation of Example 8.

The same process as used to produce the oily stick foundation of Example 8 was employed, except that a powder obtained in Comparative Example 4 was used, instead of a powder obtained in Example 4, to give a preparation of Comparative Example 7.

Example 8 and Comparative Example 7 were applied to the skin, and the resulting stains were evaluated immediately after application by vision for how notable their whiteness is. The evaluation was ranked as above. The results are shown in Table 9.

TABLE 9

| | Example 8 | Comparative Example 7 |
|---|---|---|
| Transparency | ○ | Δ |

From the results of Table 9 it is seen that Example 8 comprising a composite of Example 4 provides a foundation whose whiteness looks natural and plain even when observed immediately after its application to the skin, and thus ensures a fine finish. In contrast, Comparative Example 7 containing a powder of Comparative Example 4 gives a notable white when applied to the skin. Moreover, it is more difficult to extend Comparative Example 7 uniformly over the skin. From this it is obvious that addition of silica sol improves the dispersibility of cerium oxide as well as of titanium oxide.

Additional exemplary cosmetic preparations containing the metal oxide/silica composite of this invention will be described below.

EXAMPLE 9

W/O sunscreen

| | | |
|---|---|---|
| 1. | Talc | 6 |
| 2. | The titanium oxide/silica composite of Example 1 treated with stearic acid | 12 |
| 3. | Zinc oxide treated with stearic acid | 8 |
| 4. | Octylmethoxy cinnamate | 5 |
| 5. | Liquid petroleum | 1 |
| 6. | Decamethyl cyclopentasiloxane | 26.8 |
| 7. | Dimethyl polysiloxane | 16 |
| 8. | Polyoxyethylene modified dimethylpolysiloxane | 2 |
| 9. | Ion exchanged water | 15 |
| 10. | 1,3-butylenes glycol | 8 |
| 11. | Antiseptic | 0.1 |
| 12. | Perfume | 0.1 |

(Manufacture of a Stearic Acid-Treated Powder)

To ethanol 100 parts was added stearic acid 5 parts for dissolution. To this mixture was added a powder 20 parts for mixture. The resulting dispersion was heated with stirring at a temperature of 90° C. or higher, to allow the solvent to evaporate, which yielded a stearic acid-treated powder.

Production Method

Constituents 4 to 8 were heated at 70° C. for mixture to give an oil phase. In a separate run, constituents 10 and 11 were added to constituent 9 for dissolution to give a water phase. To the oil phase were added powdery constituents 1 to 3, and the powder was dispersed with a homogenizer. To the yield was added the water phase, which was then emulsified with a homogenizer. To the yield was added constituent 12, and the mixture was poured in a vessel.

EXAMPLE 10

Solid powder foundation

| | | |
|---|---|---|
| 1. | Silicone treated talc | 11.4 |
| 2. | Silicone treated mica | 41 |
| 3. | Silicone treated titanium dioxide | 10 |
| 4. | The titanium oxide/silica composite of Example 1 treated with silicone | 10 |
| 5. | The cerium oxide/silica composite of Example 3 treated with silicone | 8 |
| 6. | Silicone treated red iron oxide | 1 |
| 7. | Silicone treated yellow iron oxide | 3 |
| 8. | Silicone treated black iron oxide | 0.2 |
| 9. | Nylon powder | 2 |
| 10. | Dimethyl polysiloxane | 8.5 |
| 11. | Octylmethoxy cinnamate | 1 |
| 12. | Polyoxyethylene modified dimethylpolysiloxane | 0.6 |
| 13. | Polyoxyethylene sorbitan monooleate | 1 |
| 14. | Isocetyl octanoate | 2 |
| 15. | Ethyl paraben | 0.2 |
| 16. | Perfume | 0.1 |

Production Method

Constituents 10–15 were heated for dissolution (which was made an oil phase). In a separate run, constituents 1–9 were mixed with a blender, and the yield was mixed with the oil phase. Constituents 16 was sprayed into the mixture, and mixed to uniformity. The yield was pulverized with a miller, placed into a medium-sized plate, and molded under pressure.

EXAMPLE 11

W/O foundation

| | | |
|---|---|---|
| 1. | Sericite | 5 |
| 2. | Kaolin | 4 |
| 3. | Titanium dioxide | 6 |
| 4. | Red iron oxide | 0.36 |
| 5. | Yellow iron oxide | 0.8 |
| 6. | Black iron oxide | 0.16 |
| 7. | The zinc oxide/silica composite of Example 4 | 4 |
| 8. | Liquid petroleum | 5 |
| 9. | Decamethyl cyclopentasiloxane | 29 |
| 10. | Polyoxyethylene modified dimethylpolysiloxane | 4.5 |
| 11. | Ion exchanged water | 36 |
| 12. | 1,3-butylenes glycol | 5 |
| 13. | Antiseptic | 0.1 |
| 14. | Perfume | 0.08 |

Production Method

Constituents 8–10 were heated at 70–80° C. for dissolution (which was made an oil phase). In a separate run, to constituent 11 were added constituents 12 and 13 (which was made a water phase). Constituents 1–7 were mixed, to which was added the oil phase, and the yield was mixed with a homomixer. To the yield was added constituent 14 for mixture, to which was added the water phase for emulsification, and the yield was poured into a vessel.

EXAMPLE 12

Lipstick

| | | |
|---|---|---|
| 1. | The titanium oxide/silica composite of Example 2 | 10 |
| 2. | Red 201 (Lithol Rubine B (D & C Red No.6)) | 0.6 |
| 3. | Red 202 (Lithol Rubine BCA (D & C Red No.7)) | 1 |
| 4. | Red 223 (Tetrabromofluorescein (D & C Red No.21)) | 0.2 |
| 5. | Candelilla wax | 9 |
| 6. | Solid paraffin | 8 |
| 7. | Beeswax | 5 |
| 8. | Carnauba wax | 5 |
| 9. | Lanolin | 11 |
| 10. | Castor oil | 23.2 |
| 11. | 2-ethylcetylhexanoate | 17 |
| 12. | Isopropyl myristate | 10 |
| 13. | Antioxidant | suitable amount |
| 14. | Perfume | suitable amount |

Production Method

Constituents 1–3 were mixed with a part of constituent 10, and the yield was treated with a roller (the yield was made a pigment). Constituent 4 was dissolved into a part of constituent 10 (the yield was made a dye). Constituents 5–13 were mixed, and heated for dissolution, to which were added the pigment and the dye. The yield was mixed with a homomixer to such an extent as to make the constituents thereof to be uniformly dispersed. The yield was poured in a die, and suddenly cooled to give a stick-like mold.

EXAMPLE 13

W/O emulsified sunscreen (liquid type)

| | | |
|---|---|---|
| 1. | Talc | 3.0 |
| 2. | The titanium oxide/silica/alumina composite of Example 5 | 12.0 |
| 3. | Bentonite | 0.5 |

EXAMPLE 13-continued

W/O emulsified sunscreen (liquid type)

| | | |
|---|---|---|
| 4. | Polyoxyethylene sorbitan monostearate | 0.9 |
| 5. | Triethanolamine | 1.0 |
| 6. | Propylene glycol | 10.0 |
| 7. | Ion exchanged water | 51.1 |
| 8. | Stearic acid | 2.2 |
| 9. | Isohexadecyl alcohol | 7.0 |
| 10. | Glycerin monostearate | 2.0 |
| 11. | Liquid lanolin | 2.0 |
| 12. | Liquid petroleum | 8.0 |
| 13. | Antiseptic | 0.2 |
| 14. | Perfume | 0.1 |

Production Method

Constituent 3 was dispersed in constituent 6; the yield was added to constituent 7; and the yield was heated to 70° C. and then stirred with a homomixer. Then, to the yield were added constituents 4 and 5, to give a water phase. In a separate run, constituents 8–13 were heated to 70–80° C. for dissolution, to give an oil phase. To the water phase were added constituents 1 and 2 with stirring, and the yield was treated with a homomixer at 70° C. To the yield was gently added the oil phase kept at 70–80° C., and the yield was treated with a homomixer at 70° C. After cooling, the yield was mixed with constituent 14, and the yield was poured into a vessel.

According to this invention, it is possible to obtain a cosmetic preparation in which particles of metal oxide have an improved dispersibility and in which fine particles satisfactorily exert their characteristic activities such as UV protection, by adding, to a base material, a metal oxide/silica composite which is obtained by mixing fine particles of metal oxide having a primary particle diameter of 1–1000 nm with silica particles to allow the two kinds of particles to intimately disperse into each other, such that the metal oxide particles exist substantially as primary particles.

I claim:

1. A metal oxide/silica composite wherein metal oxide particles whose primary particle diameter is 1–1000 nm are co-dispersed fine with silica particles, and the metal oxide particles exist substantially as primary particles in the composite, wherein the composite is obtained by (a) mixing the dispersion with the fine particles of metal oxide or its sol, (b) altering the pH of the resulting mixture solution, and (c) exposing the resulting solution to a temperature between 80–120° C. so as to cause the silica particles to condense and the condensed silica particles and the metal oxide to aggregate for deposition
   wherein said silica particles are condensed thereby not maintaining in their initial state.

2. The metal oxide/silica composite as claimed in claim 1, wherein the composite is obtained by mixing (1) a dispersion comprising a silica sol where silica particles have a primary particle diameter of 1–150 nm, and (2) fine particles metal oxide whose primary particle diameter is 1–1000 nm, or a sol of the same metal oxide.

3. The metal oxide/silica composite as claimed in claim 1, wherein the metal oxide existing as fine particles or a sol consists of one, or two or more selected from a group consisting of titanium oxide, zinc oxide, and cerium oxide.

4. The metal oxide/silica composite as claimed in claim 1, wherein the metal oxide/silica composite exists in a gel form.

5. The metal oxide/silica composite wherein the composite is in a powdery form obtained by further drying the gel form of said metal oxide/silica composite as claimed in claim 4.

6. The metal oxide/silica composite as claimed in claim 1, wherein the composite comprises 5–90 wt % metal oxide with respect to the total weight of the composite.

7. A cosmetic preparation comprising the metal oxide/silica composite as claimed in claim 1.

8. The metal oxide/silica composite as claimed in claim 1, wherein said metal oxide particles are stably dispersed in said metal oxide/silica composite.

* * * * *